June 13, 1967 R. G. JELLY Plant Pat. 2,746
ROSE PLANT
Filed Feb. 1, 1966
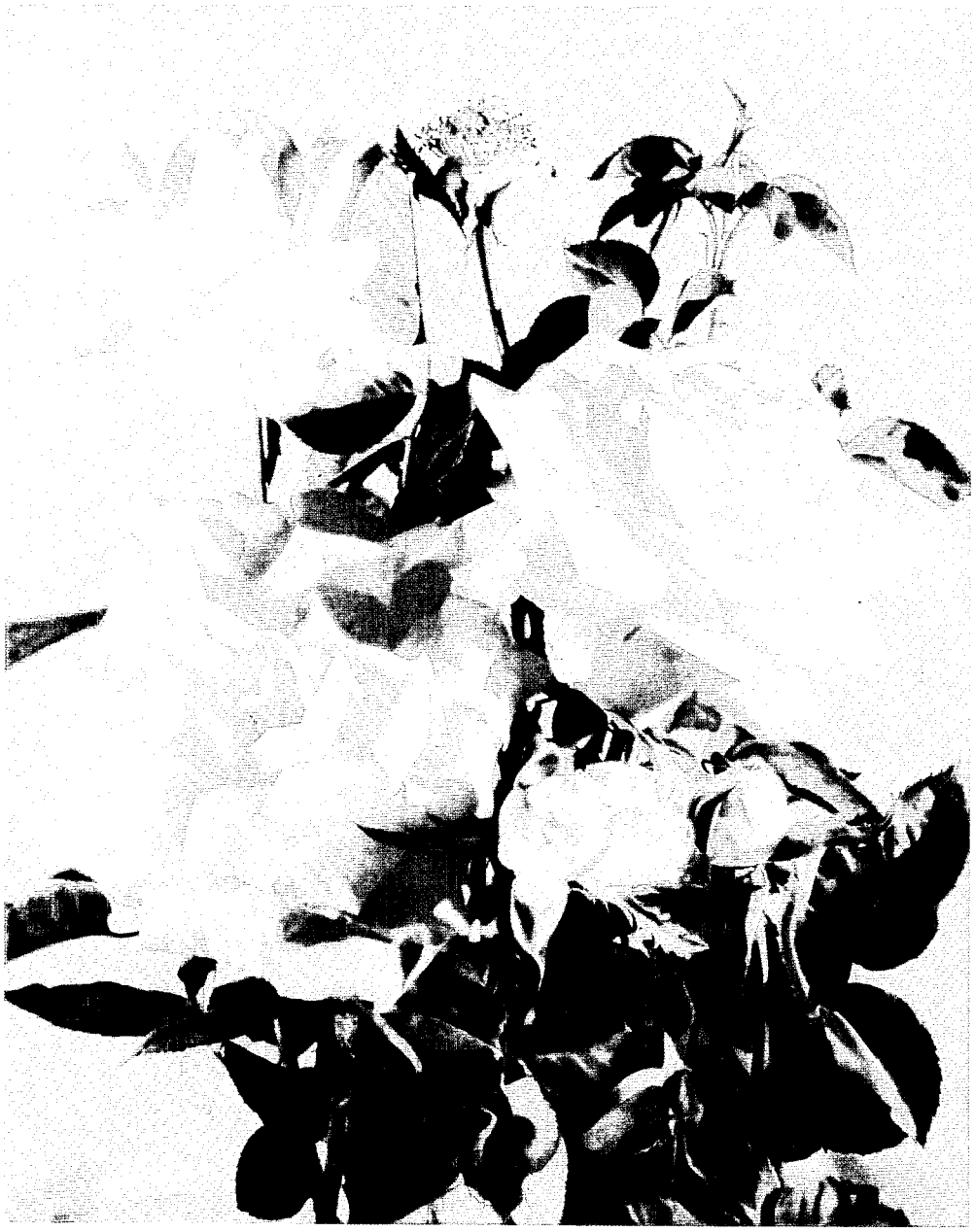
Robert G. Jelly
Inventor
Burns, Brown, Beardsley, Anderson & Kelly
Attorneys United States Patent Office Plant Pat. 2,746
Patented June 13, 1967

2,746
ROSE PLANT

Robert G. Jelly, Richmond, Ind., assignor, by mesne assignments, to The Conard-Pyle Company, West Grove, Pa., a corporation of Pennsylvania Filed Feb. 1, 1966, Ser. No. 523,809
1 Claim. (Cl. Plt.—11)

This invention relates to a new and distinct variety of rose plant of the hybrid tea class which was originated by me by crossing Peace (Plant Patent No. 591) with Dawn (Plant Patent No. 1,316).

The primary objective of this breeding was to create a distinct variety of rose different from all other known varieties of roses in several important characteristics.

This new variety may be distinguished from its seed parent, Peace, Plant Patent No. 591, in the following ways:

(1) The color of the petals is light crimson with yellow reverse whereas that of Peace is predominantly yellow.

(2) The foliage of the plant is less glossy than that of Peace.

This new variety may be distinguished from its pollen parent Dawn, Plant Patent No. 1,316, in the following ways:

(1) The color of the petals is light crimson with yellow reverse whereas that of Dawn is from spinel pink to hermosa pink.

(2) The variety is primarily suited for outdoor growing whereas Dawn is specifically for underglass growing.

Asexual reproduction of my new variety by budding was performed in West Grove, Pa.

The accompanying drawings shows typical specimens of the flowers and foliage of my new variety in different stages of development and as depicted in color as nearly true as is reasonably possible to make the same in a color illustration of this character.

The following is a detailed description of my new variety with color terminology in accordance with the horticultural color chart of the Royal Horticultural Society:

Type: Hardy; bush; outdoor; seedling; for garden decoration.
Class: Hybrid tea.
Propagation: It does hold its distinguishing characteristics through succeeding propagations by budding.

*The Flower*

Locality where grown: West Grove, Pa.
Flowers borne: Singly to stem; on normal medium to long stems.
Quantity of bloom: Free outdoors.
Continuity: Continuous.
Fragrance: Moderate; tea.
Bud:
*Peduncle.*—Medium length; medium size; erect; reddish; medium rough; medium; glandular tipped hairs; red or green.
*Before calyx breaks.*—Size—medium. Form—medium pointed ovoid; with foliaceous appendages on the surface of the bud; with slender bristle-like foliaceous parts extending beyond the tip of the bud equal to ½ or more of its length.
*As calyx breaks.*—Color—near Sap Green 62/1 at base of petal becoming shaded with Spinel Red 0023.
*As first petal opens.*—Size—medium. Form—medium; urn shaped. Color: outside—Barium Yellow 503 at base of petal fading progressively to Barium Yellow 503/2 and becoming irregularly shaded with Spinel Red 0023/2; inside—basal quarter of petal Canary Yellow 2 then becoming Canary Yellow 2/3 almost entirely overlaid with Spinel Red 0023/3.
*Opening.*—It does open up well. Buds may appear lighter during cool wet weather.

Bloom:
*Size when fully open.*—4½ inches to 6 inches.
*Petalage.*—Very double; from 45 to 50 petals; arranged regularly.
*Form.*—High centered; full and high centered; petals remaining at first loosely rolled outward; becoming later at maturity loosely rolled outward.
Petals: Medium leathery; with inside satiny; outside satiny.
*Shape.*—Outer—round; with no notches. intermediate—almost round; with no teeth. Inner—sometimes round sometimes undulate; with no notches.
*Color.*—Colors may be modified by being shaded with other colors.

This description of a newly opened flower was made from a rose grown outdoors in September 1965, at West Grove, Pa.

*Color.*—Outer petal: outside surface—Canary Yellow 2/2 at base of petal becoming progressively paler and at the same time overlaid with Crimson 22/2 reaching maximum intensity at the margin of the petal; inside surface—base of petal Canary Yellow 2 becoming lightly overlaid with Chinese Yellow 606 then changing over the upper half of the petal to Crimson between 22/3 and 22–2 with maximum intensity at margin of petal 22/2. Intermediate petal: outside surface—Canary Yellow 2/2 at base of petal fading to Naples Yellow 403 and becoming progressively overlaid with Carmine 21/2 towards the margin; inside surface—base of petal Canary Yellow 2 overlaid with Chinese Yellow 606/1 over central part of petal, becoming progressively overlaid with Rose Opal 022/2 shading to 022/1 at margin. Inner petal: outside surface—Canary Yellow 2/2 at base of petal becoming overlaid towards the margin with Carmine 21/2; inside surface—base of petal Canary Yellow 2/1 becoming overlaid with Chinese Yellow 606/1 and then over the larger part of the petal with Rose Opal 022/2 with margin of petal Rose Opal 022/1.

This description was made from a rose that was open for three days, outdoors, in September 1965, at West Grove, Pa.

*Color.*—Outer petal: outside surface—Canary Yellow 2/2 over basal quarter of petal surrounding point of attachment fading to Naples Yellow 403/1 and then to Rose Madder 23/2 at margin of the petal; inside surface—base of petal Canary Yellow 2/1 changing progressively to Chinese Yellow 606/1 and, over the major area of the petal, to Fuchsine Pink 627/2. Inner petal: outside surface—Canary Yellow 2/2 over basal quarter of petal fading to Naples Yellow 403/1 and then to Carrot Red 612/3 at the margins of the petal; inside surface—base of petal Canary Yellow 2/1 changing to Chinese Yellow 606/1 and, over the upper half of the petal, to Rose Opal 022/1.

General color effect:
*Newly opened flower.*—Crimson between 22/3 and 22/2 with reverse of petal showing Naples Yellow 403.
*Three days open.*—Fuchsine Pink 627/2 with reverse of petals showing Naples Yellow 403/1.
Behavior: Drop off cleanly.
Flower longevity: On bush in garden 5 days in September; cut roses grown outdoors kept at living room temperatures 3 days.

*Reproductive organs*

Stamens: Few to medium; arranged irregularly mixed with petaloids.

Filaments: Most with anthers; medium to long. Color—reddish-orange at base becoming yellow towards anther (general color terms).

Anthers: open at various times; medium size. Color—yellow (general color term). Occasionally an anther fused with a petaloid.

Pollen: Moderate; gold.

Pistils: Medium to many.

Styles: Uneven; medium length; medium size; bunched.

Stigma: White yellow.

Ovaries: Protruding from receptacle.

Hips: None observed.

Sepals: Permanent; medium length; spear shaped.

Seeds: None observed.

*Plant*

Foliage:

*Leaves.*—Compound of 5 leaflets; normal; medium size; leathery.

*Leaflets.*—Shape—round to almost oval with apex acute, base round, margin simple serrate.

*Color.*—Mature: upper surface—Parsley Green 00962; under surface—Lavender Green 000761. Young: upper surface—Parsley Green 00962 overlaid with Maroon 1030; under surface—Lavender Green 000761 overlaid with Erythrite Red 0027/1.

*Rachis.*—Medium. Upper side—grooved hairy with glandular tipped hairs on both edges. Under side—sparsely prickly.

*Stipules.*—Moderately long; medium; with medium points; turning out at an angle of more than 45°.

*Disease.*—Subject to mildew. Otherwise resistance comparable to the average variety growing under the same cultural conditions.

Growth:

*Habit.*—Bushy, much branched.

*Growth.*—Free.

*Canes.*—Meduim.

*Main stems.*—Dull. Color—Spinach Green 0960/2. Prickles—several; color—brown (general color term). Hair—none.

*Branches.*—Dull. Color—Spinach Green 0960/2 sometimes with a slight reddish overlay. Prickles—several; color—reddish (general color term). Hairs—none.

*New shoots.*—Dull. Color—Spinach Green 0960/2 to Fern Green 0862 sometimes with a reddish overcast. Prickles—several; color—reddish (general color term). Hairs—none.

I claim:

A new and distinct variety of rose plant of the hybrid tea class, substantially as herein shown and described, characterized particularly as to novelty by the color of the flowers, a light crimson with yellow reverse to the petals and the size and shape of the flowers, as described and illustrated, by the habit of the plant in producing most of its flowers on single stems, and the well-branched habit and moderate height.

No references cited.

ANTONIO F. GUIDA, *Acting Primary Examiner.*

ROBERT E. BAGWILL, ABRAHAM G. STONE, *Examiners.*